United States Patent [19]

Peet et al.

[11] Patent Number: 5,047,534

[45] Date of Patent: Sep. 10, 1991

[54] SELECTIVE ADENOSINE RECEPTOR AGENTS

[75] Inventors: Norton P. Peet, Cincinnati; Nelson L. Lentz, West Chester, both of Ohio

[73] Assignee: Merrell Dow Pharmaceuticals Inc., Cincinnati, Ohio

[21] Appl. No.: 499,111

[22] Filed: Mar. 26, 1990

[51] Int. Cl.[5] .................... A61K 31/52; C07D 473/12
[52] U.S. Cl. .................................. 544/267; 544/272; 544/273
[58] Field of Search ............... 514/263; 544/267, 272, 544/273

[56] References Cited

U.S. PATENT DOCUMENTS 4,772,607  9/1988  Badger et al. .................. 514/263
4,783,530  11/1988  Rzeszotarski et al. .......... 877/267

FOREIGN PATENT DOCUMENTS 081591  9/1985  European Pat. Off. .
7306507  11/1972  Netherlands .

OTHER PUBLICATIONS

H. W. Hamilton et al., J. Med. Chem. (1987), vol. 30, pp. 91-96.
K. A. Jacobson et al., Functionalized Congeners of 1,3-Dialkylxanthines: Preparation of Analogues with High Affinity for Adenosine Receptors, *J. Med. Chem.*, 28, 1334-40 (1985).
K. Hirota et al., Pyridine Derivatives and Related Compounds, *Chem. Pharm., Bull.*, 31(11), 3959-66 (1983).
K. A. Jacobson et al., Molecular Probes for Extracellular Adenosine Receptors, *Biochemical Pharm.*, 36(10), 1697-1707 (1987).
S. Senda et al., Pyrimidine Derivatives and Related Compounds, *Chem. Pharm. Bull.* 20(2), 399-403 (1972).
L. Capuano, Synthese von Thieno, Tetrahydrobenzothieno-, Pyrazolo-, Triazolo- und Pyrido-Pyrimidinen Sowie Naphth- und Thien-Oxazinen, *Chem. Ber.*, 102, 3698-3706 (1969).
EP Application 203721, Published Dec. 3, 1986, [Derwent Abstract 86-320644 provided].

*Primary Examiner*—Mukund J. Shah
*Assistant Examiner*—Matthew V. Grumbling

[57] ABSTRACT

Xanthine derivative which act selectively at adenosine receptors and which act in general as adenosine antagonists are disclosed. From in vitro studies it is known that specific physiological effects can be distinguished as a result of this selectively and that adenosine receptor activity in vitro correlates with adenosine receptor activity in vivo.

Pharmaceutical preparations of the subject compounds can be prepared on the basis of the selective binding activity of the compounds disclosed herein which will enhance certain physiological effects while minimizing others, such as decreasing blood pressure without decreasing heart rate.

18 Claims, No Drawings

SELECTIVE ADENOSINE RECEPTOR AGENTS

FIELD OF THE INVENTION

The present invention relates to a group of compounds which are xanthine derivatives and which act selectively at adenosine receptors.

BACKGROUND OF THE INVENTION

The profound hypotensive, sedative, antispasmodic, and vasodilatory actions of adenosine were first recognized over 50 years ago. Subsequently, the number of biological roles proposed for adenosine have increased considerably. The adenosine receptors appear linked in many cells to adenylate cyclase. A variety of adenosine analogues have been introduced in recent years for the study of these receptor functions. Alkylxanthines, such as caffeine and theophylline, are the best known antagonists of adenosine receptors.

Adenosine perhaps represents a general regulatory substance, since no particular cell type or tissue appears uniquely responsible for its formation. In this regard, adenosine is unlike various endocrine hormones. Nor is there any evidence for storage and release of adenosine from nerve or other cells. Thus, adenosine is unlike various neurotransmitter substances.

Adenosine might be compared as a physiological regulator to the prostaglandins. In both cases the enzymes involved in the metabolic formation are ubiquitous and appear to be responsive to alterations in the physiological state of the cell. Receptors for adenosine, like those for prostaglandins, are proving to be very widespread. Finally, both prostaglandins and adenosine appear to be involved with the regulation of functions involving calcium ions. Prostaglandins, of course, derive from membrane precursors, while adenosine derives from cytosolic precursors.

Although adenosine can affect a variety of physiological functions, particular attention has been directed over the years toward actions which might lead to clinical applications. Preeminent has been the cardiovascular effects of adenosine which lead to vasodilation and hypotension but which also lead to cardiac depression. The antilipolytic, antithrombotic and antispasmodic actions of adenosine have also received some attention. Adenosine stimulates steroidogenesis in adrenal cells, again probably via activation of adenylate cyclase. Adenosine has inhibitory effects on neurotransmission and on spontaneous activity of central neurons. Finally, the bronchoconstrictor action of adenosine and its antagonism by xanthines represents an important area of research.

It has now been recognized that there are not one but at least two classes of extracellular receptors involved in the action of adenosine. One of these has a high affinity for adenosine and at least in some cells couples to adenylate cyclase in an inhibitory manner. These have been termed by some as the A-1 receptors. The other class of receptors has a lower affinity for adenosine and in many cell types couples to adenylate cyclase in a stimulatory manner. These have been termed the A-2 receptors.

Characterization of the adenosine receptors has now been possible with a variety of structural analogues. Adenosine analogues resistant to metabolism or uptake mechanisms have become available. These are particularly valuable, since their apparent potencies will be less affected by metabolic removal from the effector system.

The adenosine analogues exhibit differing rank orders of potencies at A-1 and A-2 adenosine receptors, providing a simple method of categorizing a physiological response with respect to the nature of the adenosine receptor. The blockade of adenosine receptors (antagonism) provides another method of categorizing a response with respect to the involvement of adenosine receptors. It should be noted that the development of antagonists specific to A-1 or A-2 adenosine receptors would represent a major breakthrough in this research field and in the preparation of adenosine receptor selective pharmacological agents having specific physiological effects in animals.

SUMMARY OF THE INVENTION

The present invention relates to compounds having the following general structures:

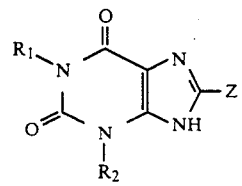

including the (R) and (S) enantiomers and racemic mixtures thereof, and the pharmaceutically acceptable salts thereof, wherein $R_1$ and $R_2$ are each independently $(C_1-C_4)$lower alkyl or $(C_2-C_4)$lower alkenyl, Z is:

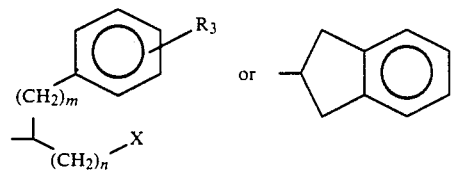

$R_3$ is $(C_1-C_3)$lower alkyl, nitro, amino, hydroxy, fluoro, bromo or chloro, m is zero or an integer from 1 to 4, n is an integer from 1 to 4, and X is H or OH.

As used in this application the term $(C_1-C_3)$lower alkyl refers to methyl, ethyl, n-propyl, or isopropyl. Also, as in this application the term $(C_1-C_4)$lower alkyl refers to methyl, ethyl, n-propyl, isopropyl, n-butyl, isobutyl, sec-butyl or tert-butyl.

In addition as used in this application the term $(C_2-C_4)$lower alkenyl refers to ethenyl, propenyl, isopropenyl, butenyl, isobutenyl, etc.

Also, as used in this application, the substituent represented by $R_3$ may be at any position from 2-6 around the phenyl ring. There may be up to three such independent substitutions around the ring wherein the substituent is other than hydrogen.

DETAILED DESCRIPTION OF THE INVENTION

In general, compounds according to the invention can be made by following the procedures described in detail in Reaction Schemes I and II below.

REACTION SCHEME I

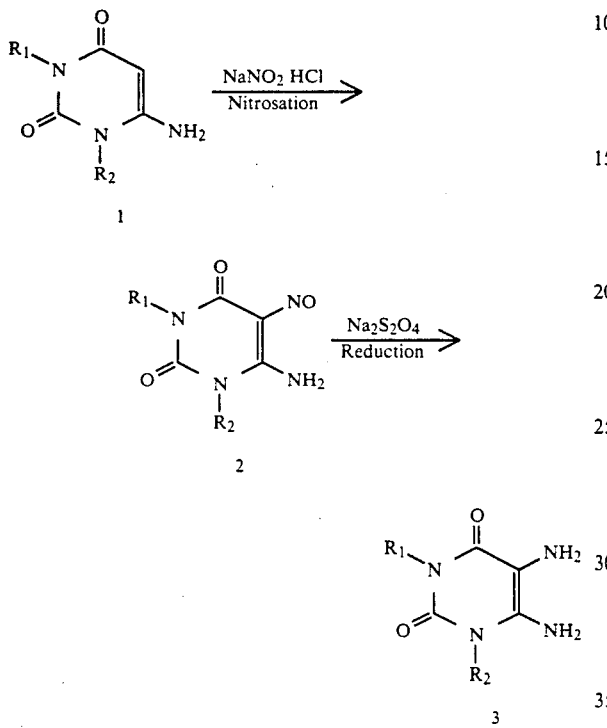

An appropriately alkyl substituted starting compound 1, 6-amino-2,4(1H,3H)-pyrimidinedione, wherein $R_1$ and $R_2$ are defined as above, is chosen so that $R_1$ and $R_2$ are defined the same as that desired in the final product.

The 6-amino-2,4(1H,3H)-pyrimidinedione is suspended in water with 20% acetic acid. Sodium nitrite (1.5 equivalents) in water is added in portions while keeping the solution mildly acidic with concentrated hydrochloric acid. The suspension is allowed to stir for several hours. It is then filtered, rinsed with water and dried under vacuum to yield the purple colored, alkyl substituted 6-amino-5-nitroso-2,4(1H,3H)-pyrimidinedione (2).

The alkyl substituted 6-amino-5-nitroso-2,4(1H,3H)-pyrimidinedione is then suspended in water, made alkaline with 50% ammonium hydroxide (pH ≈ 11) and treated with excess sodium dithionite until the purple color fades. The reaction is then extracted with chloroform. The organic extracts are combined and dried over anhydrous magnesium sulfate, filtered and concentrated under vacuum. The residue is purified by flash chromatography (5% to 10% methanol in chloroform). This material is then recrystallized from 10% isopropanol/hexane to yield the alkyl substituted 5,6-diamino-2,4-(1H,3H)-pyrimidinedione (3). (See J. W. Daly, *J. Med. Chem.*, 28, 487, 1985, incorporated herein by reference.)

Compound 3 from Scheme I is then reacted as shown in Scheme II.

REACTION SCHEME II

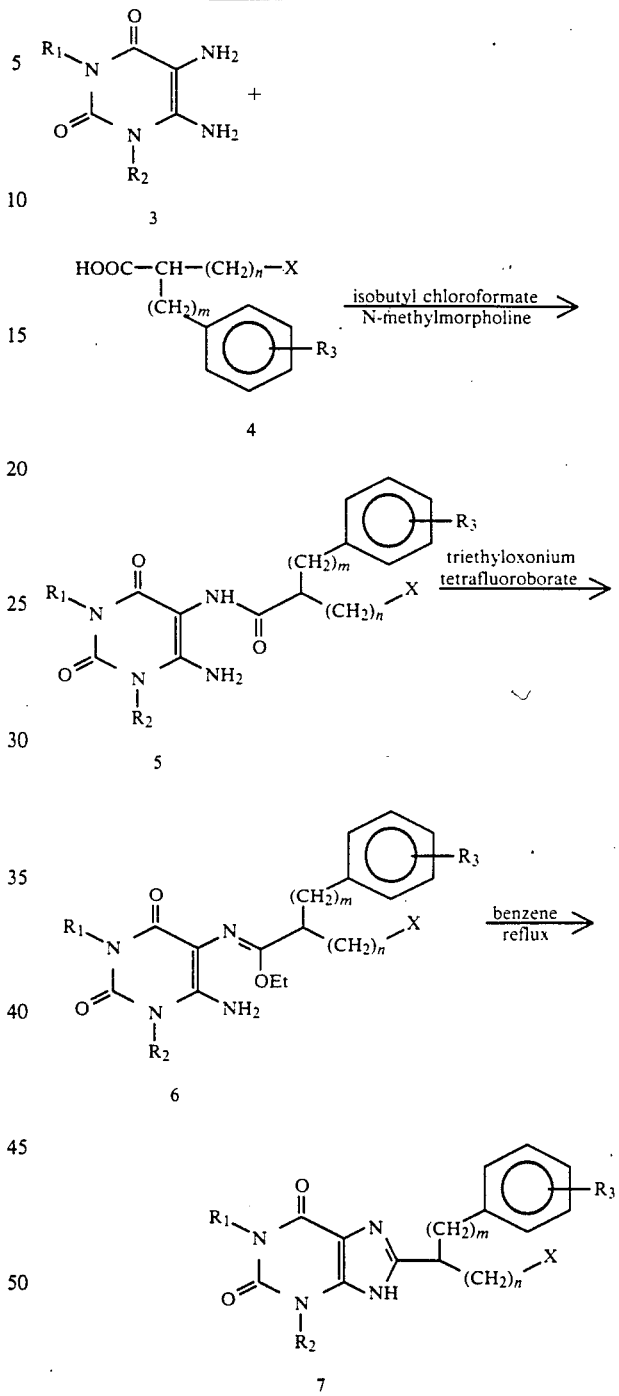

The alkyl substituted 5,6-diamino-2,4(1H,3H)-pyrimidinedione (3) is then reacted with a 2-alkyl substituted alkanoic acid (4), wherein m, n, X and $R_3$ are defined as above. The acid (4) is chosen such that the definition of m and n are the same as that desired in the final product. It should be noted that the carbon atom designated by —CH— exhibits chirality and the acid should be chosen such that the chirality is the same as that desired in the final product. Examples of such acids include the following:

S-(+)-2-phenylpropionic acid
R-(−)-2-phenylpropionic acid

In addition, other such acids can be prepared as follows:

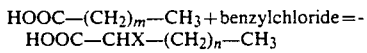

wherein m is an integer from 1 to 4, n is m-1 and X is a benzyl group of the structure

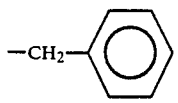

The acid is dissolved in tetrahydrofuran and treated with two equivalents of lithium diisopropylamide at room temperature. The reaction is heated to 40° C. for 30 minutes. The reaction is then treated with one equivalent of benzyl chloride and heating is continued at 40° C. for several hours. The reaction is then cooled to room temperature, poured into water and extracted with diethyl ether. The aqueous phase is then acidified with 1M hydrochloric acid and extracted with ether. The combined organic extracts are dried over anhydrous magnesium sulfate, filtered and concentrated. The residue is purified by radial chromatography (40% to 50% ethyl acetate in hexane, 2 mm plate) to yield the 2-alkyl substituted-3-phenylpropionic acid (4).

Examples of acids which can be reacted with benzyl chloride to form the 2-alkyl substituted-3-phenylpropionic acids are the following:
n-butyric acid
n-valeric acid In addition, other such acids can be prepared as shown in Scheme III.

REACTION SCHEME III

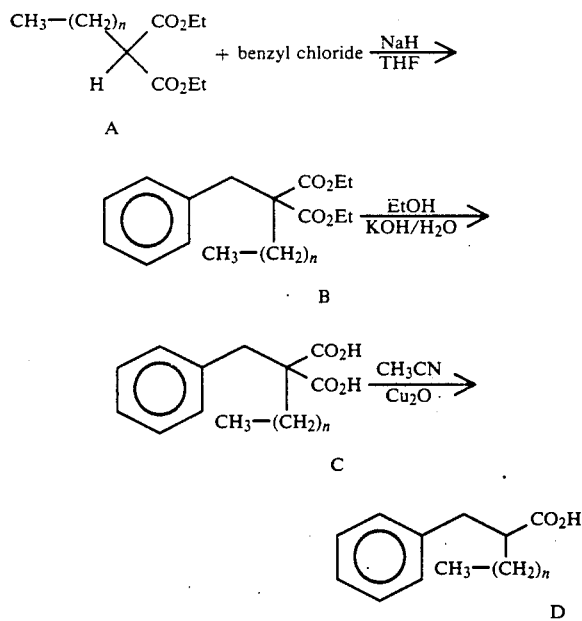

An appropriate alkyl substituted diethyl malonate (A), wherein n is defined as above is chosen such that n has the same definition as that desired in the final product. The malonate is added dropwise to a suspension of one equivalent of sodium hydride in tetrahydrofuran at 0° C. After stirring for approximately 30 minutes, one equivalent of benzyl chloride is added and the reaction is heated to reflux for approximately 3 hours. The reaction is then cooled, poured into water and extracted with ethyl acetate. The combined organic extracts are dried over anhydrous magnesium sulfate, filtered and concentrated under vacuum to yield the alkyl substituted diethyl benzylmalonate (B).

The alkyl substituted diethyl benzylmalonate (B) is then treated with aqueous potassium hydroxide in ethanol and heated to reflux for 14 hours. After cooling, the reaction is extracted with diethyl ether. The aqueous phase is then acidified with concentrated hydrochloric acid and extracted with diethyl ether. The combined organic extracts are dried over anhydrous magnesium sulfate and filtered and concentrated under vacuum to yield the alkyl substituted benzylmalonic acid (C).

The alkyl substituted benzylmalonic acid (C) is then dissolved in acetonitrile and treated with a catalytic amount of cuprous oxide. (See M. Maumy, et al., Synthesis, 1029, 1986.) It is then heated to reflux for 5 hours. The solvent is then removed under vacuum. The residue is taken up in diethyl ether and rinsed with 10% hydrochloric acid followed by rinsing with saturated sodium chloride solution. The organic extract is dried over anhydrous magnesium sulfate, filtered and concentrated under vacuum. The residue is purified by flash chromatography (5% to 10% methanol in chloroform) to yield the 2-alkyl substituted-3-phenylpropionic acid (4) (see Reaction Scheme II).

The 2-alkyl substituted-3-phenylpropionic acid (4) is then dissolved in tetrahydrofuran, treated with one equivalent of N-methylmorpholine (NMM) and cooled to −20° C. One equivalent of isobutyl chloroformate is added and the reaction is allowed to stir for approximately 30 minutes. The alkyl substituted 5,6-diamino-1,3-dipropyluracil (3) in dimethylformamide is added and the reaction is stirred at −20° C. for 4 hours. After warming to room temperature, the solvent is removed under vacuum. The residue is taken up in chloroform and rinsed with saturated sodium bicarbonate solution, followed by rinsing with saturated sodium chloride solution. The organic extract is then dried over anhydrous magnesium sulfate, filtered and concentrated under vacuum. The residue is purified by radial chromatography (3% to 5% to 10% methanol in chloroform)(10% to 15% isopropanol in hexane) to yield amide (5).

The amide (5) is then dissolved in dry benzene and treated with 6.5 equivalents of triethyloxonium tetrafluoroborate (1M in dichloromethane). The reaction is heated to 50° C. for approximately 2 hours. After cooling, the reaction is poured into phosphate buffer and extracted with diethyl ether. The organic phase is rinsed with saturated sodium chloride solution, dried over anhydrous magnesium sulfate, filtered and concentrated under vacuum. The residue is purified by radial chromatography (3% to 6% methanol in chloroform) to yield the imino ether (6).

The imino ether (6) is then dissolved in dry benzene and heated to reflux for approximately 2 hours under nitrogen. The solvent is removed under vacuum and the residue is purified by radial chromatography (50% ethyl acetate in hexane) to yield the 1,3-dialkyl-8-substituted xanthine (7).

REACTION SCHEME IV

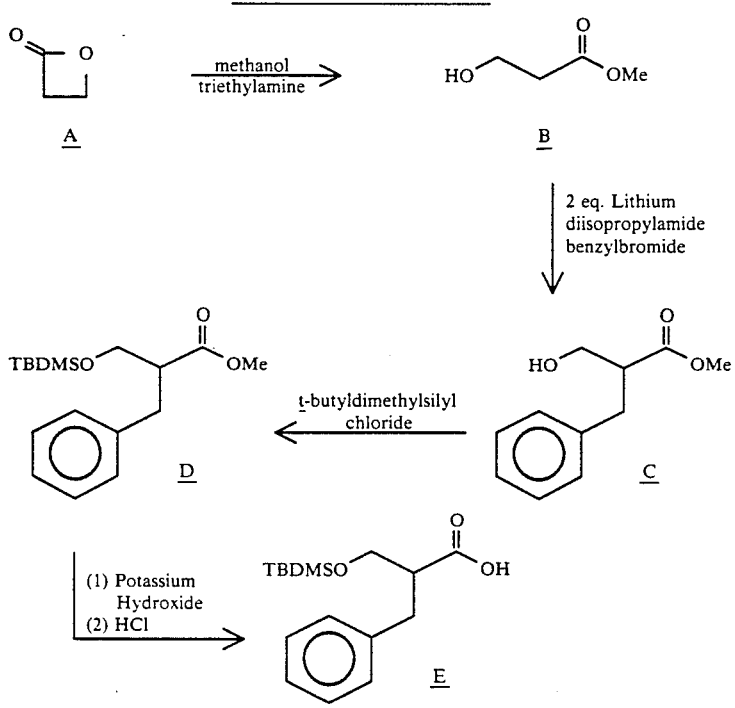

Another 2-substituted alkanoic acid can be prepared as shown in Reaction Scheme IV above.

β-Propiolactone (A) is dissolved in methanol and treated with 1 equivalent of triethylamine to produce methyl 3-hydroxypropionate (B). Compound B is converted to the dianion with 2 equivalents of lithium diisopropylamide and alkylated with 1 equivalent of benzyl bromide to produce methyl 2-benzyl-3-hydroxypropionate (C). Compound C is protected as the t-butyldimethysilyl ether (D). Compound D is then saponified with potassium hydroxide and carefully acidified to produce the acid (E). The acid (E) is then dissolved in tetrahydrofuran, treated with 1 equivalent of N-methylmorpholine and cooled to −20°. One equivalent of isobutyl chloroformate is added, followed by 1 equivalent of 5,6-diamino-1,3-dipropyluracil in dimethylformamide to produce the amide. The amide is then treated with aqueous potassium hydroxide at 70° C. to produce the cyclized, deprotected 3,7-dihydro-8-[1-(hydroxymethyl)-2-phenylethyl]-1,3-dipropyl-1H-purine-2,6-dione.

REACTION SCHEME V

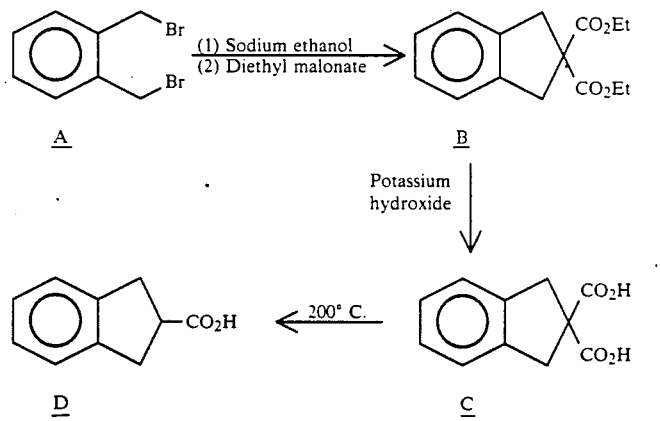

Another carboxylic acid which can be employed for the preparation of target compounds as illustrated in Reaction Scheme II can be prepared as shown in Reaction Scheme V above.

α,α-Dibromo-o-xylene (A) is treated with the anion of diethylmalonate at reflux to produce the diester (B). Compound B is then saponified with aqueous potassium hydroxide to produce compound C which is thermally decarboxylated at 200° C. to produce the indan-2-carboxylic acid (D) (see *J. Med Chem.*, 32, 1989 (1989). The acid (C) is then dissolved in tetrahydrofuran, treated with 1 equivalent of N-methyl morpholine, and cooled to −20° C. One equivalent of isobutyl chloroformate is added, followed by 1 equivalent of 5,6-diamino-1,3-dipropyluracil in dimethylformamide to produce the amide. The amide is treated with aqueous potassium hydroxide and heated to reflux to produce the cyclized product, 3,7-dihydro-8-(2-indanyl)-1,3-dipropyl-1H-purine-2,6-dione.

The following list illustrates compounds according to the present invention:

3,7-Dihydro-8-[(1R)-methyl-2-phenylethyl]-1,3-dipropyl-1H-purine-2,6-dione
3,7-Dihydro-8-[(1S)-methyl-2-phenylethyl]-1,3-dipropyl-1H-purine-2,6-dione
3,7-Dihydro-8-[(hr)-phenylethyl]-1,3-dipropyl-1H-purine-2,6-dione
3,7-Dihydro-8-[(1S)-phenylethyl]-1,3-dipropyl-1H-purine-2,6-dione
3,7-Dihydro-8-[1-(phenylmethyl)butyl]-1,3-dipropyl-1H-purine-2,6-dione
3,7-Dihydro-8-(1-phenylethyl)-1,3-di-2-propenyl-1H-purine-2,6-dione
3,7-Dihydro-8-[1-(phenylmethyl)propyl]-1,3-dipropyl-1H-purine-2,6-dione
3,7-Dihydro-8-(1-phenylethyl)-1,3-dipropyl-1H-purine-2,6-dione.
3,7-Dihydro-8-(1-phenylethyl-2-phenylethyl)-1,3-dipropyl-1H-purine-2,6-dione.
3,7-Dihydro-8-(2-indanyl)-1,3-dipropyl-1H-purine-2,6dione.
3,7-Dihydro-8-(hydroxymethyl-2-phenylethyl)-1,3-dipropyl-1H-purine-2,6-dione.
3,7-Dihydro-8-[(±)-phenylpropyl]1,3-dipropyl-1H-purine-2,6-dione.

Therapeutic Utility Of Selective Adenosine Receptor Agents

The table below shows in more detail the potential therapeutic utility of selective adenosine receptors agents in accordance with the present invention:

| Area | Effect | Receptor Correlate |
|---|---|---|
| Cardiovascular | cardiotonic | A-1 antagonism |
| Caridovascular | control tachycardia | A-1 agonism |
| Cardiovascular | increase coronary blood flow | A-2 agonism |
| Cardiovascular | vasodilation | A-2 (atypical) agonism |
| Pulmonary | bronchodilation | A-1 antagonism |
| Pulmonary | mediation of autocoid release from mast cells, basophils | novel adenosine receptor interaction on cell surface |
| Pulmonary | stimulate respiration; treat paradoxical ventilatory response (infants) | Ado antagonism |
| Renal | inhibit renin release | A-1 agonism |
| Central Nervous System | aid in opiate withdrawal | Ado agonism |
| Central Nervous System | analgesic | A-1 agonism |
| Central Nervous System | anticonvulsant | A-1 agonism |
| Central Nervous System | antidepressant | A-1 agonism |
| Central Nervous System | antipsychotic | Ado agonism |
| Central Nervous System | anxiolytic | agonism |
| Central Nervous System | inhibition of self-mutilation behavior (Lesch-Nyhan syndrome) | Ado agonism |
| Central Nervous System | sedative | A-2 agonism |

In the cardiovascular, pulmonary and renal system targets, designed compounds which are identified by receptor binding studies can be evaluated in functional in vivo tests which are directly indicative of the human physiological response. A good description of the pharmacology and functional significance of purine receptors is presented by M. in *Ann. Rev. Pharmacol. Toxicol.,* 27, 31 (1987), which is incorporated herein by reference. In a section entitled "Therapeutic Targeting of Adenosine Receptor Modulators" it is stated that "adenosine agonists may be effective as antihypertensive agents, in the treatment of opiate withdrawal, as modulators of immune competence and resin release, as antipsychotics and as hypnotics. Conversely, antagonists may be useful as central stimulants, inotropics, cardiotonics, antistress agents, antiasthmatics, and in the treatment of respiratory disorders." The smorgasbord of activities displayed by adenosine receptor agents underscores their great potential utility for therapy and the need for specific agents.

Adenosine exerts its various biological effects via action on cell-surface receptors. These adenosine receptors are of two types: A-1 and A-2. The A-1 receptors are operationally defined as those receptors at which several N6-substituted adenosine analogs such as R-phenylisopropyladenosine (R-PIA) and cycloadenosine (CHA) are more potent than 2-chloroadenosine and N-5'-ethylcarboxamidoadenosine (NECA). At A-2 receptors the order of potency is instead NECA>2-chloroadenosine>R-PIA>CHA.

As illustrated in the table above, adenosine receptors govern a variety of physiological functions. The two major classes of adenosine receptors have already been defined. These are the A-1 adenosine receptor, which is inhibitory to adenylate cyclase, and the A-2 adenosine receptor, which is stimulatory to adenylate cyclase. The A-1 receptor has a higher affinity for adenosine and adenosine analogs than the A-2 receptor. The physiological effects of adenosine and adenosine analogs are complicated by the fact that nonselective adenosine receptor agents first bind the rather ubiquitous low-affinity A-2 receptors, then as the dose is increased, the high-affinity A-2 receptors are bound, and finally, at much higher doses, the very high-affinity A-1 adenosine receptors are bound. (See J. W. Daly, et al., Subclasses of Adenosine Receptors in the Central Nervous System: Interaction with Caffeine and Related Methylxanthines, *Cellular and Molecular Neurobiology,* 3,(1), 69–80 (1983), incorporated herein by reference.)

In general, the physiological effects of adenosine are mediated by either the stimulation or the inhibition of adenylate cyclase. Activation of adenylate cyclase increases the intracellular concentration of cyclic AMP, which, in general, is recognized as an intracellular second messenger. The effects of adenosine analogs can therefore be measured by either the ability to increase or the ability to antagonize the increase in the cyclic AMP in cultured cell lines. Two important cell lines in this regard are VA 13 (WI-38 VA 13 2RA), SV-40 transformed WI 38 human fetal lung fibroblasts, which are known to carry the A-2 subtype of adenosine receptor, and fat cells, which are known to carry the A-1 subtype of adenosine receptor. (See R. F. Bruns, Adenosine Antagonism by Purines, Pteridines and Benzopteridines in Human Fibroblasts, *Chemical Pharmacology,* 30, 325–33, (1981), incorporated herein by reference.)

It is well known from in vitro studies that the carboxylic acid congener of 8-phenyl-1,3-dipropyl-xanthine (XCC) is adenosine receptor nonselective, with a Ki at the A-1 receptors in brain membranes of 58±3nM and a Ki at the A-2 receptors of the brain slice assay of 34±13nM. The amino congener of 8-phenyl-1,3-dipropyl-xanthine (XAC), on the other hand, has a 40-fold higher affinity for A-1 adenosine receptors, with a Ki of 1.2±0.5nM, as compared with a Ki at the A-2 receptors of the brain slice assay of 49±17nM. In addition, XAC is much more potent in antagonizing the effects of adenosine analogs on heart rate than on blood pressure. Since it is generally known that the adenosine analog-induced effects on the heart seem to be mediated via A-1 receptors and those on blood pressure via A-2 receptors, the selectivity of XAC under in vivo conditions suggests that adenosine receptor activity in vitro correlates with adenosine receptor activity in vivo and that specific physiological effects can be distinguished as a result of this selectivity. (See B. B. Fredholm, K. A. Jacobsen, B. Jonzon, K. L. Kirk, Y. O. Li, and J. W. Daly, Evidence That a Novel 8-Phenyl-Substituted Xanthine Derivative is a Cardioselective Adenosine Receptor Antagonist In Vivo, *Journal of Cardiovascular Pharmacology*, 9, 396-400, (1987), incorporated herein by reference and also K. A. Jacobsen, K. L. Kirk, J. W. Daly, B. Jonzon, Y. O. Li, and B. B. Fredholdm, Novel 8-Phenyl-Substituted Xanthine Derivative Is Selective Antagonist At adenosine Receptors In Vivo, *Acta Physiol. Scand.*, 341-42, (1985), incorporated herein by reference.)

It is also known that adenosine produces a marked decrease in blood pressure. This blood pressure reduction is probably dependent upon an A-2 receptor-mediated decrease in peripheral resistance. Adenosine analogs are also able to decrease heart rate. This effect is probably mediated via adenosine receptors of the A-1 subtype.

Thus, it is readily apparent that the pharmacological administration of the adenosine receptor selective adenosine analogs disclosed herein will result in selective binding to either the A-2 or the A-1 receptor, which will, in turn, selectively result in either a decrease in blood pressure or a decrease in heart rate, for example, thereby decoupling these physiological effects in vivo. The selection of such adenosine receptor selective agents can be determined by the methods described in further detail below.

Test For Affinity For Brain Adenosine A-2 Receptors

The test described below was used to determine the potency of test compounds to compete with the ligand [3H]5'-N-ethylcarboxamidoadenosine (NECA) for the adenosine A-2 receptors prepared from animal brain membranes. (See also R. R. Bruns, G. H. Lu, and T. A. Pugsley, Characterization of the A-2 Adenosine Receptor Labeled by [3H]NECA in Rat Striatal Membranes, *Mol. Pharmacol.*, 29, 331-346, (1986), incorporated herein by reference.) Young male rats (C-D strain), obtained from Charles River, are killed by decapitation and the brain was removed. Membranes for ligand binding are isolated from rat brain striatum. The tissue is homogenized in 20 vol icecold 50 mM Tris-HCl buffer (pH 7.7) using a polytron (setting for 6 to 20 seconds). The homogenate is centrifuged at 50,000 x g for 10 minutes at 4° C. The pellet is again homogenized in a polytron in 20 vol of buffer, and centrifuged as before. The pellet is finally resuspended in 40 vol of 50mM Tris-HCl (pH 7.7) per gram of original wet weight of tissue.

Incubation tubes, in triplicate, receive 100 μl of [3H]NECA (94 nM in the assay), 100 μl of 1 μM cyclohexyl adenosine (CHA), 100 μl of 100 mM $MgCl_2$, 100 μl of 1 IU/ml adenosine deaminase, 100 μl of test compounds at various concentrations over the range of $10^{-10}$ M to $10^{-4}$ M diluted with assay buffer (50 mM Tris-HCl, pH 7.7) and 0.2 μl of membrane suspension (5 mg wet weight), in a final volume of 1 ml of 50 mM Tris-HCl, pH 7.7. Incubations are carried out at 25° C. for 60 minutes. Each tube is filtered through GF/B glass fiber filters using a vacuum. The filters are rinsed two times with 5 ml of the ice-cold buffer. The membranes on the filters are transferred to scintillation vials to which 8 ml of Omnifluor with 5% Protosol is added. The filters are counted by liquid scintillation spectrometry.

Specific binding of [3H]NECA is measured as the excess over blanks run in the presence of 100 μM 2-chloroadenosine. Total membrane-bound radioactivity is about 2.5% of that added to the test tubes. Since this condition limits total binding to less than 10% of the radioactivity, the concentration of free ligand does not change appreciably during the binding assay. Specific binding to membranes is about 50% of the total bound. Protein content of the membrane suspension is determined by the method of O. H. Lowry, N. J. Rosebrough, A. L. Farr and R. J. Randall, Protein Measurements With Folin Phenol Reagent, *J. Biol. Chem.*, 193, 265-275 (1951), (incorporated herein by reference).

Displacement of [3H]NECA binding of 15% or more by a test compound is indicative of affinity for the adenosine A-2 site. The molar concentration of a compound which causes 50% inhibition of the binding of ligand is the $IC_{50}$. A value in the range of 100-1000 nM would indicate a highly potent compound.

Test For Affinity For Brain

Adenosine A-1 Receptor Binding Sites

The test described below is used to determine the potency of test compounds to compete with the ligand [3H]cycloadenosine for the Adenosine A-1 receptor prepared from rat brain membranes. Male Sprague-Dawley rats are sacrificed by decapitation and the membranes are isolated from whole animal brains. (See R. Goodman, M. Cooper, M. Gavish, and S. Synder, Guanine Nucleotide and Cation Regulation of the Binding of [3H] Diethylphenylxanthine to Adenosine A-1 Receptors in Brain Membrane, *Molecular Pharmacology*, 21, 329-335, (1982), incorporated herein by reference.)

Membranes are homogenized (using polytron setting 7 for 10 seconds) in 25 volumes of ice-cold 50 mM Tris-HCl buffer, pH 7.7. The homogenate is centrifuged at 19,000 rpm for 10 minutes at 4° C. The pellet is washed by resuspending in 25 volumes of buffer with 2 IU of adenosine deaminase per ml and incubated 30 minutes at 37° C. The homogenate is centrifuged again. The final pellet is resuspended in 25 volumes of ice-cold buffer.

The incubation tubes, in triplicate, receive 100 μl of [3H]cyclohexyladenosine, 0.8 nM in the assay, 200 μl of test compounds at various concentrations over the range of $10^{-10}$ M to $10^{-6}$ M diluted with 50 nM Tris-HCl buffer (pH 7.7), 0.2 ml of membrane suspension (8 mg wet weight) and in a final volume of 2 ml with Tris buffer. Incubations are carried out at 25° C. for 2 hours and each one is terminated within 10 seconds by filtration through a GF/B glass fiber filter using a vacuum. The membranes on the filters are transferred to scintillation vials. The filters are counted by liquid scintillation spectrometry in 8 ml of Omniflour containing 5% Protosol.

Specific binding of [3H]cycloadenosine is measured as the excess over blanks taken in the presence of $10^{-5}$ M 2-chloroadenosine. Total membrane-bound radioactivity is about 5% of that added to the test tubes. Specific binding to membranes is about 90% of the total bound. Protein content of the membrane suspension is determined by the method of Lowry, et al. Id., 265.

Displacement of [3H]cyclohexyladenosine binding of 15% or more by a test compound is indicative of affinity for the adenosine binding site.

Adenosine Receptor Binding Affinity Values Obtained Using The Above Described Test Procedures The following is a table showing the adenosine receptor binding affinities for several compounds.

| | Adenosine Receptor Binding Affinity | | |
|---|---|---|---|
| | A1 Ki | A2 Ki | A2/A1 |
| 3,7-Dihydro-8-[(S)-1-methyl-2-phenylethyl]-1,3-dipropyl-1H-purine-2,6-dione | 60.7 nm | 848 nm | 14 |
| 3,7-Dihydro-8-[(±)-1-methyl-2-phenylethyl]-1,3-dipropyl-1H-purine-2,6-dione | 32.6 nm | 644 nm | 20 |
| 3,7-Dihydro-8-[(R)-1-methyl-2-phenylethyl]-1,3-dipropyl-1H-purine-2,6-dione | 6.9 nm | 157 nm | 23 |
| 3,7-Dihydro-8-(1-phenylethyl-2-phenylethyl)-1,3-dipropyl-1H-purine-2,6-dione | 71 nm | 2,600 nm | 37 |
| 3,7-Dihydro-8-(1-phenylethyl)-1,3-di-2-propenyl-1H-purine-2,6-dione | 20 nm | 2,400 nm | 119 |
| 3,7-Dihydro-8-(1-phenylethyl)-1,3-dipropyl-1H-purine-2,6-dione | 11 nm | 1,600 nm | 150 |
| 3,7-Dihydro-8-[1-(phenylmethyl)propyl]-1,3-dipropyl-1H-purine-2,6-dione | 13,900 nm | 71,700 nm | 5 |
| 3,7-Dihydro-8-[1-(phenylmethyl)butyl]-1,3-dipropyl-1H-purine-2,6-dione | 73 nm | 608 nm | 8 |
| 3,7-Dihydro-8-(2-indanyl)-1,3-dipropyl-1H-purine-2,6-dione | 61.8 nm | 7,100 nm | 115 |
| 3,7-Dihydro-8-(hydroxymethyl-2-phenylethyl)-1,3-dipropyl-1H-purine-2,6-dione | 556 nm | 3,900 nm | 7 |
| 3,7-Dihydro-8-[(±)-phenylpropyl]-1,3-dipropyl-1H-purine-2,6-dione | 5.1 nm | 1,100 nm | 216 |
| 3,7-Dihydro-8-[(R)-phenylpropyl]-1,3-dipropyl-1H-purine-2,6-dione | 1.6 nm | 647 nm | 404 |
| 3,7-Dihydro-8-[(S)-phenylpropyl]-1,3-dipropyl-1H-purine-2,6-dione | 52 nm | 1558 nm | 30 |

The nucleotide guanosine triphosphate (GTP) has been shown to differentially affect the binding of agonists and antagonists to a variety of neurotransmitter receptors. In general, guanine nucleotides lower the affinity of agonists for receptors without a concomitant decrease in antagonist affinity. Accordingly, GTP has been shown to decrease the potency of agonists but not antagonists as inhibitors of the binding of the adenosine antagonist [3H]3-diethyl-8-phenylxanthine. In general, GTP greatly reduces the potency of purine agonists, but not antagonists as inhibitors of [3H]phenylisopropyl adenosine binding and is, therefore, an antagonists. (See L. P. Davies, S. C. Chow, J. H. Skerritt, D. J. Brown and G. A. R. Johnston, Pyrazolo[3,4-d]Pyrimidines as Adenosine Antagonists, *Life Sciences*, 34, 2117–28, (1984), incorporated herein by reference.)

Pharmaceutical Preparations of the Adenosine Receptor Agents

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the breakup and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the esthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agents and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, and alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkylbeta-aminopropionates, and 2-alkylimidazoline quarternary ammonium salts, as well as mixtures. Alternatively, the compounds of this invention can be administered by aerosolization with a suitable carrier directly into the nasal passages, or by the administration of droplets of a solution of the compounds of this invention, in an appropriate solvent, directly into the nasal passages.

The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a nonionic surfactant having a hydrophilelipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The exact amount of the compound or compounds to be employed, i.e., the amount of the subject compound or compounds sufficient to provide the desired effect, depends on various factors such as the compound employed; type of administration; the size, age and species of animal; the route, time and frequency of administration; and, the physiological effect desired. In particular cases, the amount to be administered can be ascertained by conventional range finding techniques.

The compounds are preferably administered in the form of a composition comprising the compound in admixture with a pharmaceutically acceptable carrier, i.e., a carrier which is chemically inert to the active compound and which has no detrimental side effects or toxicity under the conditions of use. Such compositions can contain from about 0.1 $\mu$g or less to 500 mg of the active compound per ml of carrier to about 99% by weight of the active compound in combination with a pharmaceutically-acceptable carrier.

The compounds may also be incorporated into any inert carrier so that they may be utilized in routine serum assays, blood levels, urine levels, etc., according to techniques well known in the art.

The compositions can be in solid forms, such as tablets, capsules, granulations, feed mixes, feed supplements and concentrates, powders, granules or the like; as well as liquid forms such as sterile injectable suspensions, orally administered suspensions or solutions. The pharmaceutically acceptable carriers can include excipients such as surface active dispersing agents, suspending agents, tableting binders, lubricants, flavors and colorants. Suitable excipients are disclosed, for example, in texts such as Remington's Pharmaceutical Manufacturing, 13 Ed., Mack Publishing Co., Easton, Pa. (1965).

The following examples are presented to illustrate the present invention but they should not be construed as limiting in any way.

EXAMPLE 1

1,3-Di-n-propyl-6-aminouracil (30 g) was suspended in 1L of water with 41 ml of 20% acetic acid and overhead stirring. Sodium nitrite (9.03 g) in 41 ml of water was added in portions, keeping the solution acidic with 12 ml concentrated hydrochloric acid. A purple precipitate formed. Addition was complete in 10 minutes and the suspension was allowed to stir for 2 hours. The solution was then filtered, and the filtrate was rinsed with water and dried under vacuum to yield 46 g of 1,3-di-n-propyl-5-nitroso-6-aminouracil.

The 1,3-di-n-propyl-5-nitroso-6-aminouracil (61.6 g) was suspended in 1L of water, and the suspension was made alkaline to pH 11 with 50% ammonium hydroxide and treated with 100 g of sodium dithionite, in portions, until the purple color faded. The aqueous mixture was extracted with chloroform (8×200 ml), dried over magnesium sulfate, filtered and concentrated. The residue was purified by flash chromatography (5/10% methanol/chloroform) and recrystallized from 10% isopropanol in hexane and recrystallized from 10% isopropanol to yield 37.29 g of 1,3-di-n-propyl-5,6-diaminouracil, m.p., 127°-128° C.

Sodium hydride (50% suspension in mineral oil, 15.2 g) was rinsed with 100 ml of tetrahydrofuran and suspended in 300 ml of tetrahydrofuran, cooled to 0° C. and 50 g diethyl methylmalonate dissolved in 75 ml of tetrahydrofuran was added dropwise over 45 minutes. After stirring for an additional 30 minutes, 36.8 ml of benzyl chloride was added, followed by 24 ml of tetrahydrofuran. The reaction was then heated to gentle reflux for 3 hours, cooled, poured into 400 ml of water and extracted with ethyl acetate (3×500 ml). The combined organic extracts were dried over magnesium sulfate, filtered and concentrated to yield 75 g of diethyl The diethyl benzylmethylmalonate (75 g) was combined with 300 ml of ethanol and a solution of 100 g potassium hydroxide in 300 ml of water and heated to a gentle reflux for 5 hours. After cooling, the mixture was extracted with diethyl ether (2×300 ml). The aqueous phase was then acidified with 120 ml concentrated hydrochloric acid, and extracted with diethyl ether (3×300 ml). The combined organic extracts were dried over magnesium sulfate, filtered and concentrated to yield 49.2 g of benzylmethylmalonic acid as a yellow solid (83% yield).

The benzylmethylmalonic acid (49.2 g) was dissolved in 400 ml of acetonitrile with 1.69 g of cuprous oxide and heated to reflux for 5 hours. The solvent was removed under vacuum. The residue was taken up in 400 ml of diethyl ether and rinsed with 10% hydrochloric acid (2×300 ml), 300 ml of saturated sodium chloride, dried over magnesium sulfate, filtered and concentrated. The residue was purified by flash chromatography (5%&o10% methanol in chloroform) to yield 38.3 g of 2-benzylpropionic acid (99% yield).

The 2-benzylpropionic acid (38.3 g) was combined with 400 ml of 50% aqueous ethanol, 83.88 g quinine.2-H$_2$O and heated on a steam bath for 20 minutes to give a clear solution. After standing overnight, the crystals which formed were collected to yield 97.37 g of quinine salt. After six additional recrystallizations from 50% aqueous ethanol, there remained 18.8 g of the quinine salt.

The quinine salt (0.34 g) was treated with 100 ml of 1M sulfuric acid and extracted with chloroform (2×100 ml). The combined organic extracts were dried over magnesium sulfate, filtered and concentrated. The residue was purified by radial chromatography (5% to 10% methanol in chloroform, 2 mm plate) to yield 89 mg of (S)-2-methyl-3-phenylpropionic acid.

A 1.0 g quantity of (S)-2-methyl-3-phenylpropionic acid was combined with 0.67 ml of N-methylmorpholine, cooled to −20° C. and treated with 0.79 ml of isobutyl chloroformate. After 15 minutes, 1.38 g of 1,3-di-n-propyl-5,6-diaminouracil in 2 ml dimethylformamide was added. The reaction was allowed to warm to room temperature over 2 hours. The reaction was then poured into 300 ml of chloroform, rinsed with 200 ml of saturated sodium bicarbonate, 200 ml of saturated sodium chloride, dried over magnesium sulfate, filtered and concentrated. The residue was purified by radial chromatography (3% to 5% to 10% methanol in chloroform, 2 mm plate) and (10% to 15% isopropyl alcohol in hexane, 2 m plate) to yield 1.6 g of amide. This was purified by flash chromatography (3% to 5% to 10% methanol in chloroform) (5% to 10% isopropyl alcohol in hexane) to yield 1.05 g of amide. This was purified by radial chromatography (5% isopropyl alcohol in hexane, 2 mm plate) to yield 0.44 g of amide.

The amide (430 mg) was dissolved in 40 ml of dry benzene and 7.5 ml of triethyloxonium tetrafluoroborate (1M in methylene chloride) was added. The reaction was heated to reflux for 5 hours. It was then poured into phosphate buffer, extracted with 300 ml toluene, dried over magnesium sulfate, filtered and concentrated. The residue was purified by radial chromatography (3% to 6% methanol in chloroform, 2 mm plate) to yield 209 mg of imino ether and 122 mg of starting material. The imino ether was again purified as above to yield 121 mg of pure chiral imino ether.

A 121 mg quantity of the chiral imino ether was dissolved in 14 ml of benzene and heated to reflux for 4 hours. Thin layer chromatography indicated complete reaction. The solvent, was removed under vacuum and the residue purified by radial chromatography (50% ethyl acetate in hexane, 2 mm plate) to yield 87 mg of material which was recrystallized from 20% diethyl ether in hexane to yield 76 mg of 3,7-dihydro-8-[(1S)-1-methyl-2-phenylethyl]-1,3-dipropyl-1H-purine-2,6-dione after drying under vacuum at 60° C. for 2 hours as a white solid, m.p. 141°-142° C.

EXAMPLE 2

S-(+)-2-Phenylpropionic acid (0.69 g), 0.46 ml of N-methylmorpholine and 10 ml of tetrahydrofuran were combined and cooled to −20° C. An 0.46 ml volume of isobutyl chloroformate was added and the reaction was allowed to stir for 25 minutes. An 0.84 g quantity of 1,3-di-n-propyl-5,6-diaminouracil in 5 ml of dimethylformamide was added and the reaction was stirred at −20° C. for 4 hours. The solution was then warmed to room temperature overnight. The solvent was removed under high vacuum and the residue was taken up in 300 ml of chloroform. The organic layer was rinsed with 200 ml of saturated sodium bicarbonate, 200 ml of saturated sodium chloride, dried over magnesium sulfate, filtered and concentrated. The residue was purified by flash chromatography (5% to 10% to 15% isopropyl alcohol in hexane) to yield 0.94 g of amide as a foam (69% yield).

The above amide (0.90 g) was dissolved in 50 ml of dry benzene, treated with 16.3 ml of triethyloxonium tetrafluoroborate (1M in methylene chloride) and heated to 50° C. for 15 hours. The solution was then poured into 300 ml of phosphate buffer and extracted with 400 ml of diethyl ether. The organic phase was rinsed with 300 ml of saturated sodium chloride, dried over magnesium sulfate, filtered and concentrated. The residue was purified by radial chromatography (3% to 5% to 10% methanol in chloroform, 2 mm plate) to yield 0.70 g of imino ether (72% yield).

The above imino ether (0.70 g) was dissolved in 50 ml of dry benzene and heated to reflux under nitrogen for 4 hours. The solvent was removed under high vacuum and the residue was purified by radial chromatography (50% ethyl acetate in hexane, 2 mm plate) to yield 0.415 g of product after recrystallization. This was dried under high vacuum over $P_2O_5$ to yield 0.413 g of product, m.p. 134.5°-136° C. This was again recrystallized from 20% diethyl ether in hexane to yield 255 mg of product which was dried under high vacuum in a drying pistol at 39° C. for 20 hours to yield 252 mg of 3,7-dihydro-8-[(1S)-1-phenylethyl]-1,3-dipropyl-1H-purine-2,,6-dione.

EXAMPLE 3

N-Valeric acid (1 g) was dissolved in 75 ml of tetrahydrofuran and treated with 2 equivalents of lithium diisopropylamide at room temperature. The solution was then heated to 40° C. for 30 minutes followed by the addition of 1.1 ml of benzyl chloride. After 1.5 hours at 40° C., the reaction mixture was cooled to room temperature, poured into 300 ml of water and extracted with diethyl ether (2×200 ml). The aqueous solution was then acidified with 1M hydrochloric acid and extracted with diethyl ether (2×300 ml). The combined organic extracts were dried over magnesium sulfate, filtered and concentrated. The residue was purified by radial chromatography (40-50% ethyl acetate in hexane, 2 mm plate) to yield 1.63 g of 2-benzylpentanoic acid (87% yield).

The 2-benzylpentanoic acid (0.88 g) was dissolved in 15 ml of tetrahydrofuran with 0.46 ml of N-methylmorpholine. The solution was cooled to −20° C. and 0.60 ml of isobutyl chloroformate was added. After 30 minutes, 0.84 g 1,3-di-n-propyl-5,6-diaminouracil in 5 ml of dimethylformamide was added with stirring at −20° C. After 3 hours, the reaction was warmed to room temperature and the solvent was removed under high vacuum. The residue was purified by flash chromatography (5% to 10% isopropyl alcohol in hexane) to yield 0.55 g of the amide as a foam.

The amide (0.55 g) was combined with 20 ml of 30% potassium hydroxide and 5 ml of ethanol and heated to 80° C. with stirring for 5 hours. The solution was then cooled, acidified with concentrated hydrochloric acid, extracted with chloroform (3×200 ml), and the organic extracts were combined and dried over magnesium sulfate. The mixture was filtered and the filtrate was concentrated under vacuum. The residue was purified by radial chromatography (50% ethyl acetate in hexane, 2 mm plate). The product was triturated with 20% diethyl ether in hexane and dried under high vacuum, at 39° C., for 16 hours to yield 217 mg of 3,7-di-hydro-8-[1-(phenylmethyl)butyl]-1,3-dipropyl-1H-purine-2,6-dione, m.p. 158°-160° C.

EXAMPLE 4

1,3-Diallyl-6-aminouracil (5 g) was suspended in 400 ml of water in a 1 L round bottom flask with overhead stirring. Acetic acid (6.7 ml of a 20% solution) was added, followed by intermittent addition of 2 ml of concentrated hydrochloric acid and a sodium nitrite solution (1.53 g in 7 ml water). After 4 hours, this solution was filtered, washed with water, collected and dried in a vacuum oven at 80° C. for 20 hours to yield 4.54 g of 1,3-diallyl-5-nitroso-6-aminouracil as a purple solid, m.p. 170°–180° C. (87% yield).

The 1,3-diallyl-5-nitroso-6-aminouracil (4.5 g) was suspended in 150 ml of ethyl acetate and treated with 23.6 g of sodium dithionite in 64 ml of water. After 1 hour, the layers were separated and the aqueous phase was extracted with ethyl acetate (4×100 ml). The combined organic extracts were dried over magnesium sulfate, filtered and concentrated and the residue was purified by flash chromatography (10% methanol in chloroform) to yield 4.41 g of 1,3-diallyl-5,6-diaminouracil.

Next, 2-phenylpropionic acid (1.0 g) was dissolved in 10 ml of acetonitrile with 0.73 ml of N-methylmorpholine at −20° C. Isobutyl chloroformate (0.86 ml) was added. After 15 minutes, 1.48 g of 1,3-diallyl-5,6-diaminouracil in 3 ml of dimethylformamide was added. After 4 hours, the reaction was warmed to room temperature and the solvent was removed under vacuum. The residue was purified twice by flash chromatography (3–5% methanol in chloroform) to yield 0.50 g of the amide.

The amide (0.50 g) was dissolved in 30 ml of dry benzene, treated with 9.2 ml of triethyloxonium tetrafluoroborate (1M in methylene chloride) and heated to 50° C. for 5 hours. After cooling, the reaction was poured into phosphate buffer (200 ml) and extracted with toluene (3×200 ml). The combined organic extracts were dried over magnesium sulfate, filtered and concentrated. The residue was dissolved in 100 ml of toluene and heated to 100° C. for 4 hours. After cooling, the solvent was removed under vacuum and the residue was purified by radial chromatography (50% ethyl acetate in hexane, 2 mm plate) to yield 0.45 g of a white solid, m.p. 142°–143° C. This solid was recrystallized from 30% diethyl ether in hexane to yield 280 mg of 3,7-dihydro-8-(1-phenylethyl)-1,3-di-2-propenyl-1H-purine-2,6-dione.

EXAMPLE 5

Diisopropylamine (3.2 ml) was dissolved in 20 ml of tetrahydrofuran, cooled to 0° C. and treated with 14.2 ml of 1.6M n-butyllithium. After 30 minutes, the lithium diisopropylamide was added to 1 g of n-butyric acid in 75 ml of tetrahydrofuran at −78° C. After 10 minutes the reaction was warmed to −20° C. After 10 more minutes the reaction was warmed slowly to room temperature. The solution was then heated to approximately 35° C. for 30 minutes and then cooled back to room temperature and 1.3 ml of benzyl chloride was added. After 1.5 hours the reaction mixture was heated to 35° C. for 2.5 hours. The solution was then cooled, diluted with 300 ml of water, rinsed with diethyl ether (2×200 ml), and the aqueous phase was acidified with 1 M hydrochloric acid and extracted with diethyl ether (3×200 ml). The combined organic extracts were dried over magnesium sulfate, filtered and concentrated. The residue was purified by radial chromatography (50% ethyl acetate in hexane, 2 mm plate) to yield 1.56 g of 2-benzylbutyric acid (77% yield).

The 2-benzylbutyric acid (0.82 g) was dissolved in 10 ml of tetrahydrofuran, cooled to −20° C., and treated with 0.46 ml of N-methylmorpholine and 0.60 ml of isobutyl chloroformate. After 30 minutes, 0.84 g of 1,3-di-n-propyl-5,6-diaminouracil in 5 ml of dimethylformamide was added and the reaction mixture was allowed to stir at −20° C. for 4 hours. The solution was then allowed to warm to room temperature overnight. The solution was then diluted with 200 ml of methylene chloride and rinsed with saturated sodium bicarbonate (100 ml). The organic phase was dried over magnesium sulfate, filtered and concentrated under high vacuum. The residue was purified by flash chromatography (5% to 10% to 15% to 20% isopropyl alcohol in hexane) to yield 1.04 g of amide (71% yield).

The amide (1.04 g) was dissolved in 10 ml of ethanol, followed by the addition of 40 ml of 30% potassium hydroxide and heated to 90° C. for 1.5 hours. The solution was then allowed to cool to room temperature overnight, and acidified with concentrated hydrochloric acid. The reaction mixture was diluted with 200 ml water, extracted with chloroform (3××200 ml), and the combined organic extracts were dried over magnesium sulfate, filtered and concentrated. The residue was purified by radial chromatography (40–50% ethyl acetate in hexane, 2 mm plate) to yield 0.49 g of product. The product was triturated with 20% diethyl ether in hexane, and the white precipitate was collected and dried at 39° C. under high vacuum to yield 418 mg of 3,7-dihydro-8-[1-(phenylmethyl)propyl]-1,3-dipropyl-1H-purine-2,6-dione, m.p. 180° C.

The above product was again dried under high vacuum at 39° C. for 6 hours to yield 407 mg of 3,7-dihydro-8-[1-(phenylmethyl)propyl]-1,3-dipropyl-1H-purine-2,6-dione, m.p. 186°–187° C. This was dried over anhydrous phosphoric acid at 39° C. under high vacuum for 24 hours to yield 342 mg of final product 3,7-dihydro-8-[1-(phenylmethyl)propyl]-1,3-dipropyl-1H-purine-2,6-dione, m.p. 186°–188° C.

EXAMPLE 6

(R)-(−)-2-Phenylpropionic acid (0.69 g) was combined with 15 ml of tetrahydrofuran, 0.46 ml of N-methylmorpholine, and cooled to -20° C. and treated with 0.6 ml of isobutyl chloroformate. After 30 minutes, 0.84 g of 1,3-di-n-propyl-5,6-diaminouracil in 5 ml of dimethylformamide was added to the reaction, which was allowed to stir at −30° C. for 4 hours. The solution was then allowed to warm to room temperature over 15 hours and the solvent was removed under hi9h vacuum. The residue was taken up in 300 ml of chloroform, and the organic phase was rinsed with 200 ml of saturated sodium bicarbonate, dried over magnesium sulfate, filtered and concentrated. The residue was purified by flash chromatography (5% to 10% to 15% to 20% isopropyl alcohol in hexane) to yield 1.21 9 of the desired amide (89% yield).

The amide (1.1 9) was dissolved in 50 ml of benzene, treated with 19.9 ml of triethyloxonium tetrafluoroborate (1M in methylene chloride) and heated at 50° C. for 15 hours. The mixture was then cooled, poured into 300 ml of diethyl ether and rinsed with 200 ml of phosphate buffer, and 200 ml of water, 200 ml of saturated sodium chloride. The organic phase was dried over magnesium sulfate, filtered and concentrated. The residue was purified by radial chromatography (2% to 5% methanol in chloroform, 2 mm plate) to yield 0.65 g of desired imino ether.

The imino ether (0.65 g) was dissolved in 60 ml of dry benzene and heated at reflux for 4 hours. After cooling, the solvent was removed under vacuum and the residue was purified by radial chromatography (50% ethyl acetate in hexane, 2 mm plate) to yield 0.56 g of 3,7- dihydro-8-[(1R)1-phenylethyl]-1,3-dipropyl-1H-purine-2,6-dione, m.p. 136°-137° C.

EXAMPLE 7

2-Phenylpropionic acid (0.69 g) was dissolved in 15 ml of tetrahydrofuran, treated with 0.46 ml of N-methylmorpholine, cooled to −20° C. and 0.6 ml of isobutyl chloroformate was added. After 30 minutes, 0.84 g of 1,3-di-n-propyl-5,6-diaminouracil in 5 ml of dimethylformamide was added. The reaction was allowed to stir at −20° C. for 4 hours and then warmed to room temperature. The solvent was removed under high vacuum and the residue was purified by flash chromatography (5% to 10% to 15% to 20% isopropyl alcohol in hexane) to yield 0.96 g of desired amide (70% yield).

The amide (0.95 g) was combined with 10 ml of ethanol and 40 ml of 30% of aqueous potassium hydroxide and heated to 90° C. for 1.5 hours. The solution was then cooled in an ice bath and carefully acidified with concentrated hydrochloric acid. The reaction mixture was diluted with 100 ml of water and the aqueous layer was extracted with chloroform (3×200 ml). The combined organic extracts were dried over magnesium sulfate, filtered and concentrated to yield 0.91 g of product. The product was purified by radial chromatography (50% ethyl acetate in hexane, 2 mm plate) to yield 0.78 g of material which was recrystallized from 20% diethyl ether in hexane to yield 0.591 g of 3,7-dihydro-8-(1-phenylethyl)-1,3-dipropyl-1H-purine-2,6-dione, m.p. 148°-150° C.

EXAMPLE 8

Sodium hydride (15.2 g, 50% solution) was rinsed with 100 ml of tetrahydrofuran. It was then suspended in 300 ml of tetrahydrofuran, cooled to 0° C. and 50 g of diethyl methylmalonate dissolved in 75 ml of tetrahydrofuran was added dropwise over 45 minutes. After stirring an additional 30 minutes, 36.8 ml of benzyl chloride was added followed by 25 ml of tetrahydrofuran. The reaction mixture was then heated at gentle reflux for 3 hours, cooled, poured into 500 ml of water and extracted with ethyl acetate (3×500 ml). The filtered and concentrated to yield 75 g of diethyl benzylmethylmalonate.

The diethyl benzylmethylmalonate (75 g) was combined with 300 ml of ethanol and a solution of 100 g of potassium hydroxide in 300 ml of water and heated at gentle reflux for 5 hours. After cooling, the mixture was extracted with diethyl ether (2×300 ml). The aqueous layer was then acidified with 120 ml of concentrated hydrochloric acid and extracted with diethyl ether (3×300 ml). The combined organic extracts were dried over magnesium sulfate, filtered and concentrated to yield 49.2 g of benzylmethylmalonic acid as a yellow solid (83% yield).

The benzylmethylmalonic acid (49.2 g) was dissolved in 400 ml of acetonitrile, treated with 1.69 g of cuprous oxide and heated to reflux for 5 hours. The solvent was removed under vacuum and the residue taken up in 400 ml of diethyl ether and rinsed with 10% hydrochloric acid (2×300 ml), saturated sodium chloride (300 ml), dried over magnesium sulfate, filtered and concentrated. The residue was purified by flash chromatography (5% to 10% methanol in chloroform) to yield 38.37 g of 2-benzylpropionic acid (99% yield).

The 2-benzylpropionic acid (38.3 g) was combined with 400 ml of 50% aqueous ethanol, 83.88 g of quinine.2H$_2$O and heated on a steam bath for 20 minutes to give a clear solution. After standing overnight, the crystals which formed were collected to yield 97.37 g of the quinine salt. After six additional recrystallizations from 50% aqueous ethanol there remained 18.8 g of the quinine salt.

The mother liquors from the above recrystallizations were acidified and extracted to yield 24.86 g of recovered 2-benzylpropionic acid. This acid was combined with 18.4 g of d-(+)-α-methylbenzylamine in 160 ml of ethyl acetate, dissolved by heating on a steam bath, cooled, and the precipitate was collected to yield 35 g of the amine salt. After three additional recrystallizations from ethyl acetate, the amine salt (0.4 g) was treated with 100 ml of 1M sulfuric acid. The aqueous layer was extracted with chloroform (2 x 100 ml) and the combined organic extracts dried over magnesium sulfate, filtered and concentrated. The residue was purified by radial chromatography (5% methanol in chloroform, 2 mm plate) to yield 186 mg of (R)-2-benzylpropionic acid.

(R)-2-Benzylpropionic acid (0.69 g) was dissolved in 15 ml of tetrahydrofuran and the solution was cooled to −20° C. and treated with 0.46 ml of N-methylmorpholine, 0.60 ml of isobutyl chloroformate and allowed to stir for 30 minutes. This was followed by the addition of 0.84 g of 1,3-di-n-propyl-5,6-diaminouracil in 5 ml of dimethylformamide and the reaction mixture was allowed to stir for an additional 4 hours at −20° C. The solution was allowed to warm to room temperature overnight. The solvent was removed under high vacuum and the purple residue was purified by flash chromatography (5% to 10% to 15% to 20% isopropyl alcohol in hexane) to yield 0.87 g of desired amide (64% yield).

The amide (0.85 g) was dissolved in 100 ml of dry benzene, treated with 14.8 ml of triethyloxonium tetrafluoroborate (1M in methylene chloride) and the solution was heated at 50° C. for 15 hours. The solution was then cooled, poured into 500 ml of diethyl ether and rinsed with 300 ml of phosphate buffer, 200 ml of saturated sodium chloride, dried over magnesium sulfate, filtered and concentrated. The residue was purified by radial chromatography (2% to 5% methanol in chloroform, 2 mm plate) to yield 0.36 g of desired imino ether.

The imino ether (0.36 g) was dissolved in 100 ml of dry benzene and heated to reflux for 3 hours. The solvent was removed under vacuum and the residue was purified by radial chromatography (50% ethyl acetate in hexane, 2 mm plate) to yield 0.23 g of 3,7-dihydro-8-[(1R)-1-methyl-2-phenylethyl]-1,3-dipropyl-1H-purine-2,6-dione. This solid was recrystallized from 20% diethyl ether in hexane to yield, after drying under high vacuum at 39° C., 187 mg of 3,7-dihydro-8-[(1R)-1-methyl-2-phenylethyl]-1,3-dipropyl-1H-purine-2,6-dione, m.p. 141°-142° C.

EXAMPLE 9

β-Propiolactone (5.5 g) was dissolved in 100 ml of methanol and treated with 10.8 ml of triethylamine at room temperature with stirring. After 3 days, the solvent was removed under vacuum and the residue was purified by flash chromatography (10% to 20% isopropyl alcohol in hexane) to yield 3.30 g of 3-hydroxymethyl propionate.

The 3-hydroxymethyl propionate (3.23 g) was dissolved in 100 ml tetrahydrofuran, cooled to −50° C. and treated with 2.1 eq. of lithium diisopropylamide in 100 ml tetrahydrofuran. After 20 minutes, 3.68 ml of benzyl bromide was added to the dianion at −50° C. The temperature was warmed to −20 ° C. over one hour. The reaction was then diluted with 500 ml of saturated ammonium chloride and the aqueous layer which formed was extracted with diethyl ether (2×500 ml). The combined organic extracts were dried over anhydrous magnesium sulfate, filtered, and concentrated. The crude residue was purified by flash chromatography (10% to 20% isopropyl alcohol in hexane) to yield 2.65 g of 2-benzyl-3-hydroxymethyl propionate.

The 2-benzyl-3-hydroxymethyl propionate (2.6 g) was dissolved in 75 ml of dry dimethylformamide under nitrogen. t-Butyldimethylsilyl chloride (2.2 g) was added with stirring, followed by the addition of 2.0 g of imidazole. After 1½ hours the reaction was diluted with 500 ml of diethyl ether. The organic phase was rinsed with 50% aqueous sodium chloride ( 3×200 ml), saturated sodium chloride (300 ml), dried over anhydrous magnesium sulfate, filtered, and concentrated under vacuum. The residue was purified by flash chromatography (5% to 10% isopropyl alcohol in hexane) to yield 3.49 g of methyl 2-benzyl-3-(t-butyldimethylsilyloxy)-propionate.

The methyl 2-benzyl-3-(t-butyldimethylsilyloxy)propionate (3.3 g) was dissolved in 100 ml of methanol, cooled to 0° C. and treated with 50 ml of 30% potassium hydroxide with vigorous stirring. The reaction was then allowed to warm to room temperature over five hours. The reaction was diluted with 200 ml of water, rinsed with diethyl ether, and the aqueous solution was cooled to 0° C. Dichloromethane (100 ml) was added, followed by the slow addition of 260 ml of 1M hydrochloric acid, with stirring. The layers were separated and the aqueous layer was extracted with dichloromethane (3×200 ml). The combined organic extracts were dried over anhydrous magnesium sulfate, filtered, and concentrated under vacuum. The residue was purified by radial chromatography (2% to 4% methyl alcohol in chloroform. 4 mm plate) to yield 2.14 9 of the 2-benzyl-3-(t-butyldimethylsilyloxy)propionic acid.

The 2-benzyl-3-(t-butyldimethylsilyloxy)propionic acid (2.1 g) was dissolved in 20 ml of tetrahydrofuran, cooled to −20 ° C. and treated with 0.71 ml of N-methylmorpholine. Isobutyl chloroformate (0.92 ml) was then added and the reaction was allowed to stir for 20 minutes at −20 ° C. The 1,3-di-n-propyl-5,6-diaminouracil (1.62 g) in 10 ml of dimethylformamide was added and the reaction was stirred for 3 hours at −20 ° C. The reaction was then warmed to room temperature, diluted with 400 ml of chloroform and the organic phase rinsed with 50% aqueous sodium chloride (2 x 200 ml), saturated sodium bicarbonate (200 ml), dried over anhydrous magnesium sulfate, filtered, and concentrated under vacuum. The residue was purified by radial chromatography (5% to 10% methyl alcohol in chloroform, 4 mm plate) to yield 4.25 g of the amide.

The amide (3.1 g) was then dissolved in 50 ml of ethyl alcohol and treated with 100 ml of 30% potassium hydroxide. This was heated to reflux for 1.5 hours. After cooling to 0° C., the reaction was acidified with 42 ml of concentrated hydrochloric acid. The aqueous layer was extracted with chloroform (2×200 ml). The combined organic extracts were dried over anhydrous magnesium sulfate, filtered, and concentrated under vacuum. The residue was purified by radial chromatography (5% to 10% methyl alcohol in chloroform, 4 mm plate) and (5% to 10% to 20% isopropyl alcohol in hexane, 4 mm plate) to yield 1.1 g of crude material. This was triturated with 25% diethyl ether in hexane to yield 0.82 g of 3,7-dihydro-8-[1-(hydroxymethyl)-2-phenylethyl]-1,3-dipropyl-1H-purine-2,6-dione as a white solid, after drying under vacuum at 39° C. for 5 hours, m.p. 145°–146° C.

EXAMPLE 10

Sodium (3.7 g) was dissolved in 80 ml of ethyl alcohol, followed by the addition of 150 ml of diethyl ether. Diethyl malonate (12.5 ml) was added followed by 20 g of α,α'-dibromo-o-xylene in 150 ml of diethyl ether with overhead stirring. The reaction was heated to reflux for 5 hours. The reaction was cooled, filtered, and the solvent was removed under vacuum. The residue was treated with a potassium hydroxide solution (20 g in 125 ml of water) and heated to reflux for 15 hours. The reaction was then cooled and rinsed with 200 ml of diethyl ether. The aqueous phase was acidified with 30% hydrochloric acid. The precipitate was collected and dried under vacuum over Drieruite for 5 hours to yield 8.86 g of indan-2,2-dicarboxylic acid.

The indan-2,2-dicarboxylic acid (8.86 g) was placed in a 500 ml, round-bottom flask and heated to 200° C. with stirring for 15 minutes. The reaction was then cooled to room temperature and recrystallized from 10% isopropyl alcohol in hexane to yield 1.77 g of indan-2-carboxylic acid. (See *J. Med. Chem.* 23, 1995, 1989.)

The indan-2-carboxylic acid (1.0 g) was dissolved in 15 ml of tetrahydrofuran, treated with 0.62 ml of N-methylmorpholine, and cooled to −20 ° C. Isobutyl chloroformate (0.80 ml) was added and the reaction was stirred for 30 minutes at −20 ° C. The 1,3-di-n-propyl-5,6-diaminouracil (1.2 g) in 5 ml of dimethylformamide was then added and the reaction was stirred at −20 ° C. for 4 hours. After warming to room temperature, the reaction was poured into 300 ml of chloroform and rinsed with 50% aqueous sodium chloride (2×100 ml), saturated sodium bicarbonate (2×100 ml), dried over anhydrous magnesium sulfate, filtered, and concentrated under vacuum. The residue was purified by radial chromatography (5% to 10% methyl alcohol in chloroform, 4 mm plate) and (10% to 20% to isopropyl alcohol in hexane, 4 mm plate) to yield 2.19 g of the amide.

The amide (2.19 g) was treated with 100 ml of 30% potassium hydroxide, 40 ml of ethyl alcohol and heated to reflux for 2 hours. The reaction was then cooled to 0° C. and acidified with 42 ml of concentrated hydrochloric acid. The precipitate was collected and dissolved in 300 ml of chloroform. The organic phase was rinsed with 200 ml of saturated sodium bicarbonate, dried over anhydrous magnesium sulfate, filtered, and concentrated under vacuum. The residue was triturated with 80% diethyl ether in hexane to yield, after drying under vacuum at 60° C., 1.10 g of 3,7-dihydro-8-(2-indanyl)-1,3-dipropyl-1H-purine-2,5-dione, m.p. 223°–224° C.

EXAMPLE 11

2-Phenylbutyric acid (1.1 g) was treated with 5,6-diamino-1,3-dipropyluracil to obtain the amide and was cyclized following the procedure in Example 7 to obtain 454 mg of 3,7-dihydro-8-[(±)-phenylpropyl]-1,3-dipropyl-1H-purine-2,6-dione, m.p. 137°–138° C.

EXAMPLE 12

(S)-(+)-2-Phenylbutyric acid (0.93 g) was treated with 5,6-diamino-1,3-dipropyluracil to obtain the amide, following the procedure in Example 6. The amide was converted to the imino ether, which was thermally cyclized following the procedure of Example 6 to obtain 547 mg of 3,7-dihydro-8-[(S)-phenylpropyl]-1,3-dipropyl-1H-purine-2,5-dione, m.p. 128°–131° C.

EXAMPLE 13

(R)-(−)-2-Phenylbutyric acid (0.98 g) was treated with 5,6-diamino-1,3-dipropyluracil to obtain the amide, following the procedure in Example 6. The amide was converted to the imino ether which was thermally cyclized following the procedure of Example 6 to obtain 190 mg of 3,7-dihydro-8-[(R)-phenylpropyl]-1,3-dipropyl-1H-purine-2,6-dione, m.p. 128°–130° C.

EXAMPLE 14

A 1.9 g quantity of 2-benzylpropanoic acid was treated with 0.65 g of potassium hydroxide in 60 ml of water, with stirring. To this solution was added 2.0 g of 5,6-diamino-1,3-dimethyluracil hydrate followed by 2.3 g of 1-ethyl-3-[3-(dimethylamino)propyl]carbodiimide hydrochloride. After 2 hours, the solvent was removed and the residue purified by radial chromatography (40% isopropyl alcohol in hexane, 4 mm plate) to yield 1.85 g of material which was triturated with ether to yield 0.40 g of amide as a white solid.

The amide (0.33 g) was treated with 10 ml of 30% aqueous potassium hydroxide and 2 ml of ethyl alcohol and heated to 70° C. for 1.5 hours. After cooling, the reaction was acidified with 55 ml of 1M hydrochloric acid and extracted with 300 ml of ethyl ether. The organic phase was rinsed with 200 ml of water, 200 ml of saturated sodium chloride, dried over anhydrous magnesium sulfate, filtered, and concentrated. The residue was triturated with hexane to yield, after drying under vacuum over phosphorous pentaoxide, 142 mg of 3,7-dihydro-8-[(±)-(methyl-2-phenylethyl)]-1,3-dimethyl-1H-purine-2,6-dione, m.p. 198°–199° C.

EXAMPLE 15

A 22 g quantity of 4-benzyloxybenzyl chloride was treated with diethyl methylmalonate anion following the procedure in Example 8. The alkylated methylmalonate was saponified and decarboxylated following the same procedure to obtain 18.06 g of 2-(4-benzyloxybenzyl)propionic acid, m p. 93°–95° C. A 3.6 g quantity of this acid was treated with 5,6-diamino-1,3-dipropyluracil to obtain the amide and was cyclized following the procedure in Example 7 to obtain 1.46 g of material which was recrystallized from 5% ethyl ether in hexane to yield 0.72 g of 3,7-dihydro-8-[methyl-2-( 4-benzyloxyphenyl)ethyl]-1,3-dipropyl-1H-purine-2,6-dione, m.p. 124°–126° C. A 260 mg quantity of 3,7-dihydro-8-[methyl-2-(4-benzyloxyphenyl)ethyl]-1,3-dipropyl-1H-purine-2,6-dione was dissolved in 20 ml of methyl alcohol and treated with a catalytic amount of 5% palladium on charcoal. This was placed under an atmosphere of hydrogen for 2 hours with stirring. It was then filtered through Celite and the filtrate concentrated under vacuum. The residue was purified by radial chromatography (50% ethyl acetate in hexane, 4 mm plate) to yield 182 mg of material which was triturated with 5% ethyl ether in hexane to yield, after drying under high vacuum at 39° C. for 3 hours, 162 mg of 3,7-dihydro-8-[methyl-2-(4-hydroxyphenyl)ethyl]-1,3-dipropyl-1H-purine-2,6-dione, m.p. 218°–220° C.

What is claimed is:

1. A compound according to the structure:

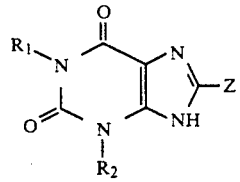

including the (R) and (S) enantiomers and racemic mixtures thereof, and the pharmaceutically acceptable salts thereof, wherein $R_1$ and $R_2$ are each independently $C_1$-$C_4$ lower alkyl or $(C_2$-$C_4)$ lower alkenyl, Z is:

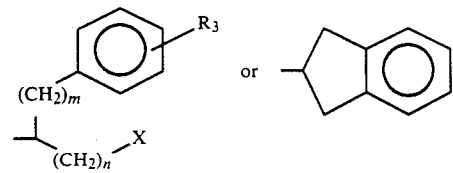

$R_3$ is $(C_1$-$C_3)$ lower alkyl, nitro, amino, hydroxy, fluoro, bromo or chloro, m is zero or an integer from 1 to 4, n is an integer from 1 to 4, and X is H or OH.

2. A compound according to claim 1 which is 3,7-dihydro-8-[(1R)-methyl-2-phenylethyl]-1,3-dipropyl-1H-purine-2,6-dione.

3. A compound according to claim 1 which is 3,7-dihydro-8-[(1S)-methyl-2-phenylethyl]-1,3-dipropyl-1H-purine-2,6dione.

4. A compound according to claim 1 which is 3,7-dihydro-8-[(1R)-phenylethyl]-1,3-dipropyl-1H-purine-2,6-dione.

5. A compound according to claim 1 which is 3,7-dihydro-8-[(1S)-phenylethyl]-1,3-dipropyl-1H-purine-2,6-dione.

6. A compound according to claim 1 which is 3,7-dihydro-8-[1-(phenylmethyl)butyl]-1,3-dipropyl-1H-purine-2,6-dione.

7. A compound according to claim 1 which is 3,7-dihydro-8-(1-phenylethyl)-1,3-di-2-propenyl-1H-purine-2,6-dione.

8. A compound according to claim 1 which is 3,7-dihydro-8-[1-(phenylmethyl)propyl]-1,3-dipropyl-1H-purine-2,6-dione.

9. A compound according to claim 1 which is 3,7-dihydro-8-(1-phenylethyl)-1,3-dipropyl-1H-purine-2,6-dione.

10. A compound according to claim 1 which is 3,7-dihydro-8-[1-(hydroxymethyl)-2-phenylethyl]-1,3-dipropyl-1H-purine-2,6-dione.

11. A compound according to claim 1 which is 3,7-dihydro-8-(2-indanyl)-1,3-dipropyl-1H-purine-2,6-dione.

12. A compound according to claim 1 which is 3,7-dihydro-8-[(±)-phenylpropyl]-1,3-dipropyl-1H-purine-2,6dione.

13. A compound according to claim 1 which is 3,7-dihydro-8-[(R)-phenylpropyl]-1,3-dipropyl-1H-purine-2,6dione.

14. A compound according to claim 1 which is 3,7-dihydro-8-[(S)-phenylpropyl]-1,3-dipropyl-1H-purine-2,6dione.

15. A compound according to claim 1 which is 3,7-dihydro-8-[(±)-methyl-2-phenylethyl]-1,3-dimethyl-1H-purine-2,6-dione.

16. A compound according to claim 1 which is 3,7-dihydro-8-[methyl-2-(4-hydroxyphenyl)ethyl]-1,3-dipropyl-1H-purine-2,6-dione.

17. A pharmaceutical composition comprising a therapeutically effective amount of a compound of claim 1 in admixture with a biologically inert carrier.

18. A pharmaceutical composition comprising a therapeutically effective amount of a compound of claim 1 in admixture with a pharmaceutically acceptable carrier.

* * * * *